(12) United States Patent
Tu et al.

(10) Patent No.: US 6,179,789 B1
(45) Date of Patent: Jan. 30, 2001

(54) ENHANCED RADIOACTIVE STENT FOR REDUCTION OF RESTENOSIS

(76) Inventors: Lily Chen Tu; Hosheng Tu, both of 2151 Palermo, Tustin, CA (US) 92782

( * ) Notice: Under 35 U.S.C. 154(b), the term of this patent shall be extended for 0 days.

(21) Appl. No.: 09/304,598

(22) Filed: May 3, 1999

(51) Int. Cl.[7] .................................................. A61B 5/00
(52) U.S. Cl. ................................ 600/585; 600/2; 600/3
(58) Field of Search ................................. 600/585, 433, 600/434, 436, 1, 2; 606/108, 194, 195, 198

(56) References Cited

U.S. PATENT DOCUMENTS

| | | | |
|---|---|---|---|
| 5,807,398 | * | 9/1998 | Shaknovich .......................... 606/108 |
| 5,871,437 | * | 2/1999 | Alt ........................................... 600/3 |
| 5,906,636 | * | 5/1999 | Casscells, III et al. ............... 607/96 |
| 6,074,338 | * | 6/2000 | Popowski et al. ....................... 600/3 |

* cited by examiner

Primary Examiner—Cary O'Connor
Assistant Examiner—Pamela L. Wingood

(57) ABSTRACT

An ablation apparatus system for treating tissues or atherosclerosis on a patient having a stent or a metallic implant, wherein said stent or metallic implant comprises a coating layer including a carrier composed of a biocompatible material and having dispersed therein a radioactive substance, the ablation apparatus system comprising an electrical conducting wire that is coupled to an external radiofrequency generator for delivering the radiofrequency current to the stent or the metallic implant for the purposes of thermally enhanced irradiation capability for tissue therapeutic treatment.

20 Claims, 4 Drawing Sheets

ENHANCED RADIOACTIVE STENT FOR REDUCTION OF RESTENOSIS

TECHNICAL FIELD OF THE INVENTION

The present invention generally relates to improved medical apparatus and methods for treating vascular tissues. More particularly, the invention relates to enhanced radioactive stents and methods for use in maintaining a lumen of a blood vessel in which the stent is implanted to expand and maintain the enlarged vessel in a patient by delivering therapeutic RF energy through a metallic stent containing radioactive element for enhanced reduction of restenosis.

BACKGROUND OF THE INVENTION

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. The benefits of angioplasty of arteries have been amply demonstrated.

There are limitations, however, to this technique's application, depending on the extent of the disease, the blood flow through the artery, and the part of the anatomy and the particular vessels involved. Plaque build-up and/or severe re-stenosis recur at about 40–50 percent of those treated. A huge number of patients experiencing a successful primary angioplasty procedure are destined to require a repeat procedure. Balloon angioplasty can only be characterized as a moderate-success procedure.

Recently, a newer technique of inserting a metallic stent is used to permanently maintain the walls of the vessel treated at its extended opening state. Vascular stents are typically composed of a biocompatible material such as a biocompatible metal wire of tubular shape, a metallic perforated tube, or a tiny mesh tube used by heart surgeons to prop open the weak inner walls of diseased arteries. The stent should be of sufficient strength and rigidity to maintain its shape after deployment, and to resist the elastic recoil of the artery that occurs after the vessel wall has been stretched. The stents are often used in conjunction with balloon angioplasty to prevent restenosis after the clogged arteries are treated. Despite of its considerable benefits, coronary stenting alone is not a panacea, as studies have shown that about 30% of the patient population subjected to that procedure will still experience restenosis. Risks of inflammation of the vessel walls are exacerbated by the presence of the stent.

When a clogged artery is widened, the plaque is broken up and the underlying collagen or damaged endothelium is exposed to the blood flow. Collagen has a prothrombotic property which is part of a body healing process. Unless collagen or the damaged endothelium is passivated, treated, or modulated, the chance for blood vessel clotting as well as restenosis still exists. Several U.S. patents disclose incorporation of drugs or radioactive elements onto the stent for slow release into the blood stream. One example is U.S. Pat. No. 5,843,163 to Wall who discloses an expandable stent having radioactive treatment means. Another example is U.S. Pat. No. 5,882,291 to Bradshaw et al. who discloses a device and methods for controlling dose rate during intravascular radiotherapy. U.S. Pat. No. 5,871,436 to Eury discloses radiation therapy method by immersing the device in a solution of the radioisotope just prior to device implantation. However, none of the above-mentioned patents disclose releasing therapeutic agents into the tissue, instead to the blood stream, at the stent contact site.

A metallic stent is generally coated with a biodegradable or non-degradable coating which incorporates a radioactive source. One particular example is U.S. Pat. No. 5,871,437 to Alt who discloses a radioactive stent for treating blood vessels to prevent restenosis. Said patent discloses that not only the restenosis triggered by the proliferation of smooth muscle cells is inhibited by a radioactive material, but the restenosis triggered by thrombus formation is also inhibited, by incorporating into the coating carrier hirudin, iloprost or other anti-coagulant. However, due to continuous blood flow to wash away the active ingredient inside the coating layer from the coated stent, the anti-restenosis effect diminishes quickly or compromised greatly. There is a clinical need to diffuse or embed the active ingredient, such as radioactive elements, anti-coagulant and the like, into the lesion site where the stent contacts the tissue of the arterial wall. An appropriate thermal energy plays a critical role in enhancing the diffusion process of an active ingredient into the tissue wall.

Radiofrequency therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. A stent deployed within a vessel, such as a coronary stent, has excellent metal-to-tissue contact surface. It becomes an ideal medium for applying thermal energy to the tissue needed for impregnation or embedding of active ingredients, such as radioactive substances or anti-coagulants. Radiofrequency protocol, which exposes a patient to minimal side effects and risks, is generally applied precisely to the stent-to-tissue contact site to obtain the desired thermal effect to accelerate the diffusion and embedding of an active ingredient into the local stent-contact tissue for prolonged therapeutic effects.

SUMMARY OF THE INVENTION

In general, it is an object of the present invention to provide a method and an improved medical apparatus for generating heat, to treat the atherosclerosis, vascular vessels, or other tissues, such as intestine, colon, ureter, uterine tube, and the like. It is another object of the present invention to provide a vascular stent having radioactive substances on the exposed surface of the stent. It is a further object of the present invention to provide a metallic implant having radioactive substances on its surface for enhanced irradiation. It is still another object to provide a medical apparatus system having radiofrequency energy to accelerate diffusing or embedding the radioactive substance into the tissue. It is another object of the present invention to provide a method and an apparatus for monitoring the temperature of the ablated tissue, and to control the temperature by utilizing a temperature control mechanism and/or algorithm for radiofrequency energy delivery. The location of the temperature sensor means is preferably at close proximity of the exposed surface of the stent apparatus or at a distal end of detachable conducting wire means. It is still another object of this invention to provide a method and an apparatus for treating atherosclerosis, vascular walls, or tubular cellular tissues in a patient by applying RF current to a stent having radioactive substance and consequently to the underlying tissues for enhanced irradiation.

Briefly, heat is generated by supplying a suitable energy source to an apparatus, which comprises electrical conductor means, in contact with the body tissues through a stent. A stent is defined in this invention as any metallic stenting element, in mesh form, coil form, perforated form, or other appropriate form, used to enlarge and maintain the enlarged tissues or vessels. Examples include coronary stent, peripheral stent, uterine stent and the like. A suitable energy source may consist of radiofrequency energy, microwave energy, ultrasonic energy, alternating current energy, or laser energy. The energy can be applied to the stent and consequently to the atherosclerosis, vascular walls, or cellular tissues through the electrode means. A DIP (dispersive indifferent pad) type returning pad or electrode, that contacts the patient, is connected to the Indifferent Electrode Connector on the RF generator. Therefore, the RF energy delivery becomes effective when a close circuit from a RF generator through a patient and returning to the RF generator is formed. The tissue behaves like a "resistor" to the RF circuit, whereby heat is generated at the stent-to-tissue contact site. The coating layer at the exposed surface of the stent is thereafter heated and releases the active ingredient inside the coating layer to the tissue via diffusion or embedding process with assistance of enhanced thermal energy. The thermally enhanced active ingredient could not diffuse to the metal side of the stent.

When using an alternating current outlet, the generator should be grounded to avoid electrical interference. Heat is controlled by the power of the RF energy delivered, the contact surface area, and by the delivery duration. The standard RF energy generator means and its applications through the electrode means, to a patient are well known for those who are skilled in the art.

In one embodiment, an ablation apparatus system comprises a vascular stent, wherein the vascular stent comprises a non-radioactive elongated metallic tube having open ends, and a sidewall containing a multiplicity of openings therethrough to allow said stent to be expanded radially for deployment in a blood vessel subjected to angioplasty so as to maintain the lumen of blood vessel open; wherein a thin coating on an exterior surface of the tube, said coating including a carrier composed of a biocompatible material and having dispersed therein a radioactive substance. The apparatus system further comprises detachable conducting wire means for detachably contact said tube, said detachable conducting wire means having a wire distal end and a wire proximal end, wherein the wire distal end is to contact the elongated metallic tube and the wire proximal end is coupled to a radiofrequency current source. The system further comprises a radiofrequency current generating means for generating radiofrequency current, wherein the radiofrequency current is transmitted to the vascular stent through the detachable conducting wire means so that the radioactive substance has thermally enhanced irradiation capability for tissue treatment. The biocompatible material for the coating may be a biodegradable material, a non-biodegradable material, or a thermally degradable material.

The ablation apparatus system may further comprise at least one temperature sensor, wherein the temperature sensor is disposed at close proximity of the wire distal end or on the elongated metallic tube. The apparatus system may further comprise temperature control means for controlling a temperature sensed from the at least one temperature sensor, wherein the temperature measured from the temperature sensor is relayed to the temperature control means and is adapted to effect the radiofrequency current delivery to the vascular stent. The radiofrequency current is preferably within the range of 50 to 2,000 kHz. The detachable conducting wire means may be selected from the group consisting of a guidewire, a spiral wire, a catheter wire, a catheter probe having an electrical conducting wire, a combination of the above-mentioned wires thereof, and the like.

In a preferred embodiment, a method of preventing restenosis of a blood vessel which has undergone angioplasty to open a restricted region of a lumen of the vessel is disclosed. The method comprises inserting a stent into the blood vessel and deploying the stent to contact the vessel wall at the site of the restricted region; irradiating the tissue in the wall at said site with a radioactive substance in a coated layer which is coated to an exterior surface of the stent; and providing radiofrequency current from a radiofrequency current generator to the stent through an electrical conducting wire so that the radioactive substance has thermally enhanced irradiation for tissue treatment.

In an alternate preferred embodiment, method for treating tissues of a patient having a metallic implant is disclosed, said metallic implant having a thin coating on an exposed surface of said implant and said coating including a carrier composed of a biocompatible material and having dispersed therein a radioactive substance. The method comprises the steps of (a) inserting detachable conducting wire means for detachably contact said metallic implant, said detachable conducting wire means having a wire distal end and a wire proximal end, wherein the wire distal end is to contact the metallic implant and the wire proximal end is to be coupled to a radiofrequency current source; and (b) applying radiofrequency current from a radiofrequency current generating means to the metallic implant through the detachable conducting wire means so that the radioactive substance has thermally enhanced irradiation for tissue treatment.

The metallic implant may be a stent, a heart valve, an orthopedic implant, and the like. The metallic implant has a coated layer composed of thermally degradable or biodegradable material so that the radioactive substance is being embedded in the tissue by the assistance of the thermal energy.

The method and medical apparatus of the present invention has several significant advantages over other known systems or techniques to treat the atherosclerosis or tissues having a stent or a metallic implant. In particular, the apparatus system comprising the detachable conducting wire means, using RF energy as a heat source, in this invention results in a more efficient therapeutic effect, which is highly desirable in its intended application on the atherosclerosis or on other tissue ablation applications when there is a pre-implanted stent.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 4, what is shown is an embodiment of the ablation apparatus system comprising a vascular stent and/or a metallic implant, wherein a thin layer is coated on its exterior surface and a radioactive substance dispersed inside the thin layer has thermally enhanced irradiation for tissue treatment.

Figure 1:
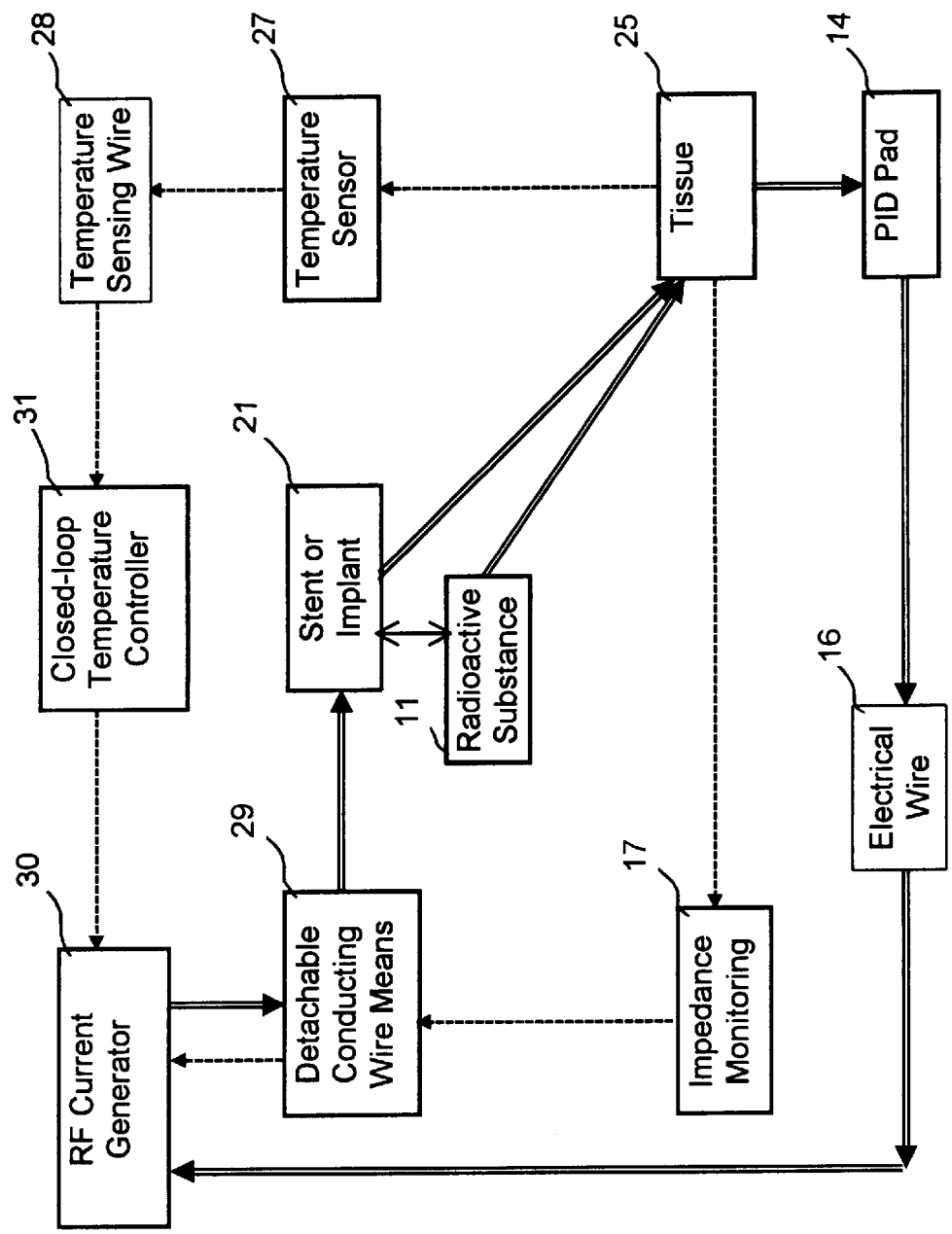
FIG. 1 is a schematic diagram of a RF treatment method in relation to the tissues through a stent or an implant having radioactive substance at its exposed surface layer.

FIG. 1 shows a schematic diagram of a RF treatment method in relation to the tissues through a stent or an implant having radioactive substance at its exposed surface layer in a patient. A RF current generator 30 is connected to a stent or an implant 21 through a detachable conducting wire means 29. The detachable conducting wire means 29 may be selected from the group consisting of a guidewire, a spiral wire, a catheter wire, a catheter probe having an electrical conducting wire, a combination of the abovementioned wires thereof, and the like. The detachable conducting wire means comprises a wire distal end and a wire proximal end, wherein the wire distal end is conductive and is in an appropriate form to effect the easy, secure, and efficient contact to the stent or implant of the present invention. The conducting wire means itself, except the wire distal end, is electrically non-conductive.

The detachable conducting wire means 29 is to contact a stent or an implant 21 when the ablation apparatus system is deployed. The stent is in close contact with the underlying tissue 25. A thin layer 12 is coated or attached on the original exterior surface 13A of the non-radioactive stent so that the exposed surface of the thin layer 13 will contact the tissue. In a stent, the exposed surface having a layer of radioactive substance is the exterior surface 13. The thin layer contains radioactive substance 11 for irradiation purposes. A DIP (dispersive indifferent pad) type pad 14, that contacts a patient, is connected to the Indifferent Electrode Connector on the RF generator 30 through a returning electrical wire 16. Therefore, the RF energy delivery becomes effective when a close circuit from a RF generator through a patient and returning to the RF generator is formed. Impedance 17 measured from the tissue contact 25 is to ensure good tissue contact for ablation, otherwise the RF current is cutoff when the impedance is unreasonably high. A temperature sensor 27 is also used to measure the tissue temperature and is relayed through a temperature sensing wire 28 and a closed-loop temperature controller 31 for controlling the ablative energy delivered. Heat is controlled by the power of the RF energy delivered and by the delivery duration. In one embodiment, the closed-loop temperature controller 31 is part of RF current generating means 30 for temperature controlling purposes.

Figure 2:
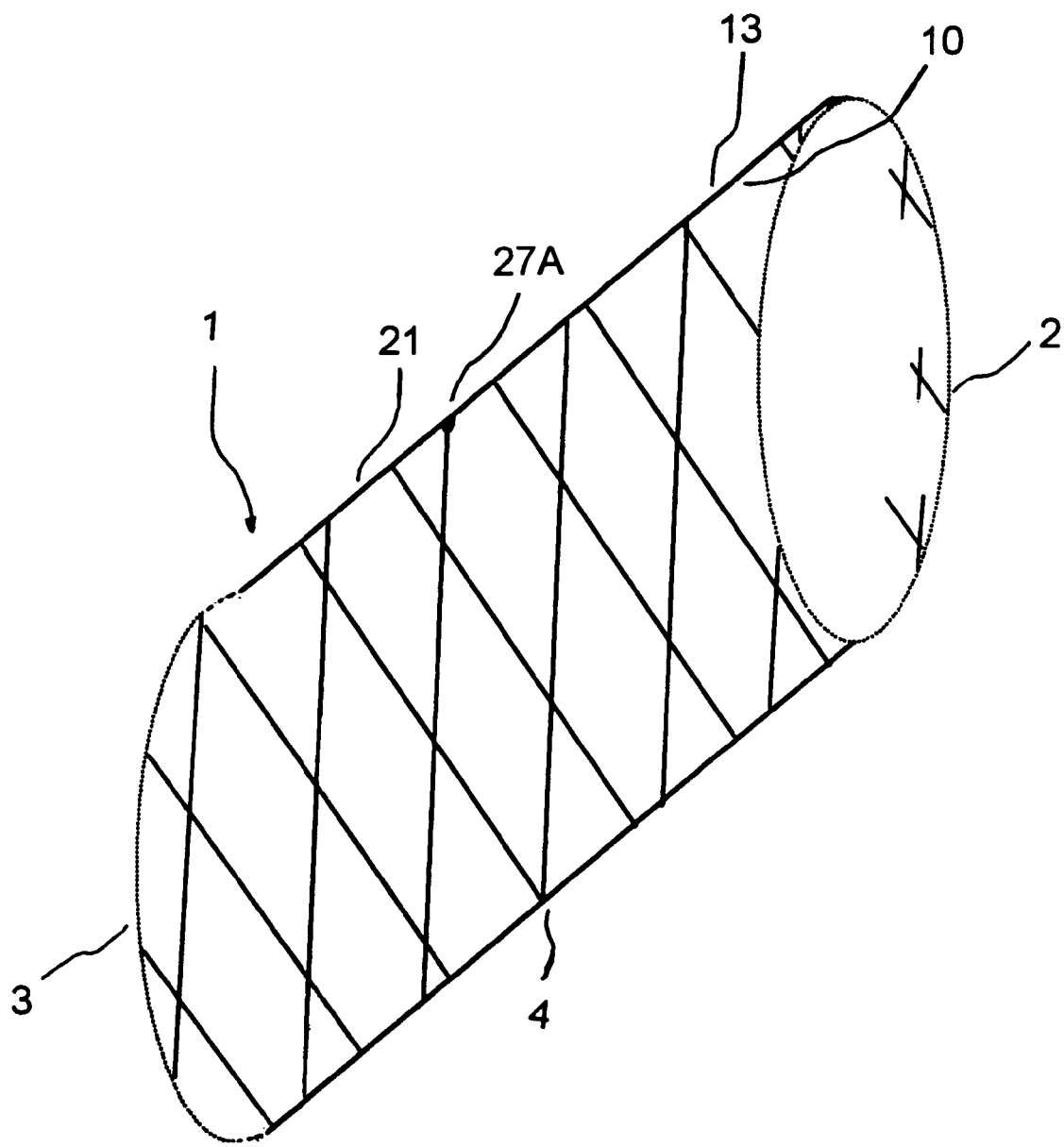
FIG. 2 is an overall view of a preferred stent having radioactive substance at its exposed surface layer, constructed in accordance with the principles of the present invention.

FIG. 2 shows an overall view of a preferred stent having radioactive substance at its exterior exposed surface layer, constructed in accordance to the principles of the present invention. In a preferred embodiment, a vascular stent 21 comprises a non-radioactive elongated metallic tube 1 having open ends 2, 3, and a sidewall 4 containing a multiplicity of openings therethrough to allow said stent to be expanded radially for deployment in a blood vessel subjected to angioplasty so as to maintain the lumen of blood vessel open; wherein a thin coating 12 on an original exterior surface 13A of the tube 1, said coating including a carrier composed of a biocompatible material and having dispersed therein a radioactive substance 11. The interior surface 10 of the tube 1 may not contain radioactive substance because the blood stream passing the interior surface 10 could sweep away the substance, if any, quickly. A vascular stent of different constructions is well known to one who is skilled in the art of stent development and design.

Figure 3:
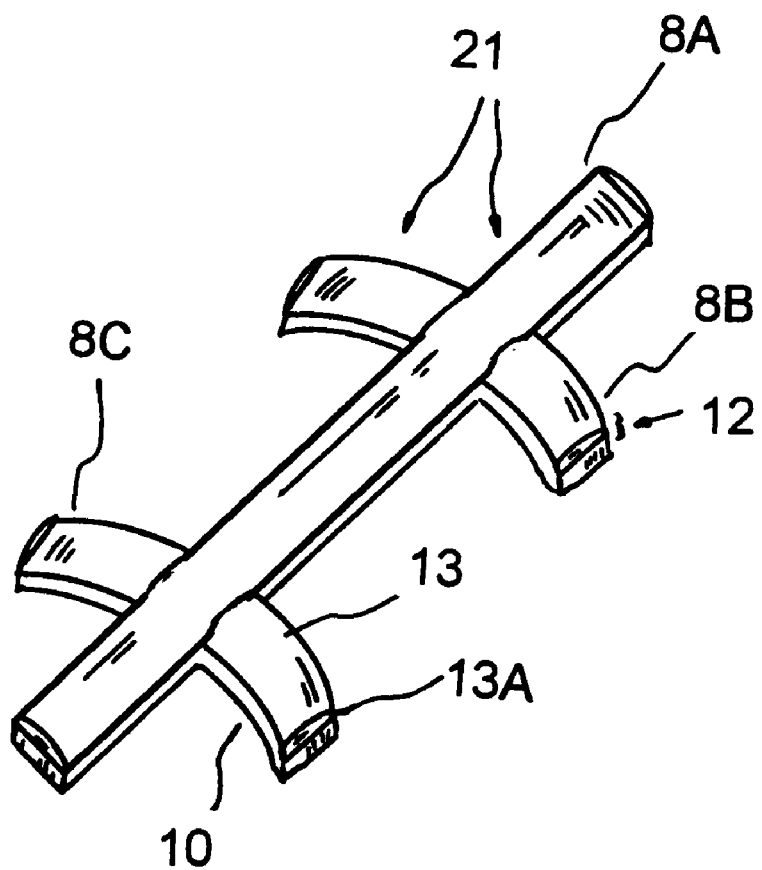
FIG. 3 is a cross-sectional perspective view of the stent and its coated layer at the exterior exposed surface of said stent.

FIG. 3 shows a cross-sectional perspective view of the stent and its coated layer at the exterior exposed surface of said stent. The stent has a plurality of wire branches 8A, 8B, 8C or meshes coupled to each other. The stent may also contain multiplicity of openings therethrough. For illustration purposes, each wire branch 8A, 8B, 8C has an interior exposed surface 10 and an original exterior surface 13A, wherein a thin layer of less than 100 microns is adhered to the original exterior surface 13A to make it as an exterior exposed surface 13. The adherence of a thin layer to the stent wire branches may be done by coating, dip coating, adhering, painting, and the like. The layer may compose any biocompatible material selected from the group of biodegradable polymer, thermally degradable material, and non-degradable material.

Figure 4:
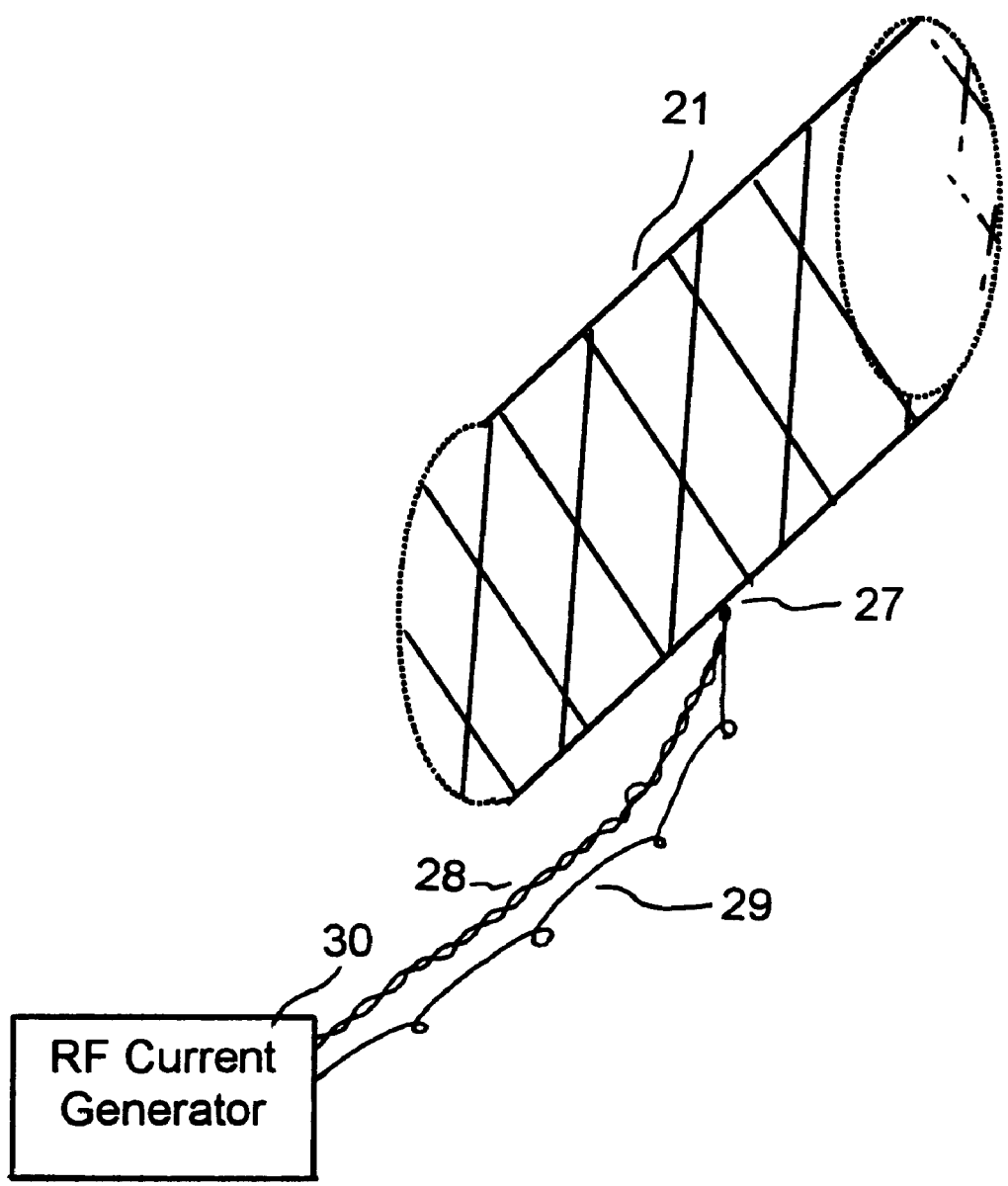
FIG. 4 is an ablation apparatus system comprising a stent having radioactive substance layer, detachable conducting wire means and a RF current generator, wherein the radioactive substance has thermally enhanced irradiation for tissue treatment.

FIG. 4 shows an ablation apparatus system comprising a stent 21 having radioactive substance layer at the exterior surface of the wire branches of the tube 1, detachable conducting wire means 29 and a RF current generator 30, wherein the radioactive substance has thermally enhanced irradiation capability for tissue treatment.

In one embodiment, at least one temperature sensing means 27 is disposed at a distal end of said conducting wire means 29. In another embodiment, a temperature sensor 27A is disposed on the elongated metallic tube 1 or at the exterior surface of the stent 21. The temperature sensor can be a thermocouple type or a thermister type. Insulated temperature sensing wire 28 passes from the temperature sensing means 27, to an external temperature control mechanism 31. The RF energy delivery is controlled by using the measured temperature from the temperature sensing means 27, through a closed-loop temperature control mechanism 31 and/or algorithm. When the measured temperature rises to the preset high-limit point, the temperature control mechanism sends out a signal to cut off the RF current supply. In a similar manner, when the measured temperature drops to the preset low-limit point, the temperature control mechanism sends out a signal to activate the RF current supply.

In one preferred embodiment, a method of preventing restenosis of a blood vessel which has undergone angioplasty to open a restricted region of a lumen of the vessel is disclosed, the method comprising (1) inserting a stent into the blood vessel and deploying the stent to contact the vessel wall at the site of the restricted region; (2) irradiating the tissue in the wall at said site with a radioactive substance in a coated layer which is coated to an exterior surface of the stent; and (3) providing radiofrequency current from a radiofrequency current generator to the stent through an electrical conducting wire so that the radioactive substance has thermally enhanced irradiation capability for tissue treatment.

As an alternative illustration, a method for treating tissues of a patient having a metallic implant is disclosed, said metallic implant having a thin coating on an exposed surface of said implant and said coating including a carrier composed of a biocompatible material and having dispersed therein a radioactive substance. The method comprises the steps of (1) inserting detachable conducting wire means for detachably contact said metallic implant, said detachable conducting wire means having a wire distal end and a wire proximal end, wherein the wire distal end is to contact the metallic implant and the wire proximal end is to be coupled to a radiofrequency current source; and (2) applying radiofrequency current from a radiofrequency current generating means to the metallic implant through the detachable conducting wire means so that the radioactive substance has thermally enhanced irradiation capability for tissue treatment.

The external RF current generating means has the capability to supply RF current by controlling the time, power, and temperature through an optional separate closed-loop temperature control means. The patient is connected to the RF generator means through a DIP electrode to form a closed-loop current system. Therefore, RF current is applied and delivered to the targeted atherosclerosis region, through the detachable conducting wire means of this invention. The radiofrequency current in this invention is preferably within the range of 50 to 2,000 kHz. By providing thermal energy to the thin layer through radiofrequency principles, the active ingredient, such as radioactive substance or anticoagulant, diffuses more quickly into the surrounding contact tissue for prolonged radiotherapy.

In a particular embodiment, the material for the stent or metallic implant of this invention may be selected from the group consisting of platinum, iridium, gold, silver, tungsten, stainless steel, Nitinol, or an alloy of these metals.

From the foregoing description, it should now be appreciated that an ablation apparatus system for the tubular organs, atherosclerosis, and the treatment of vascular tissues, comprising a suitable energy source and a layer of radioactive substance has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation apparatus system comprising:
   a vascular stent, wherein the vascular stent comprises a non-radioactive elongated metallic tube having open ends, and a sidewall containing a multiplicity of openings therethrough to allow said stent to be expanded radially for deployment in a blood vessel subjected to angioplasty so as to maintain the lumen of blood vessel open; wherein a thin coating on an exterior surface of the tube, said coating including a carrier composed of a biocompatible material and having dispersed therein a radioactive substance;
   detachable conducting wire means for detachably contacting said tube, said detachable conducting wire means having a wire distal end and a wire proximal end, wherein the wire distal end is to contact the elongated metallic tube and the wire proximal end is coupled to a radiofrequency current source; and
   a radiofrequency current generating means for generating radiofrequency current and for generating heat within the tissue, wherein the radiofrequency current is transmitted to the vascular stent through the detachable conducting wire means so that the radioactive substance diffuses more quickly into the heated tissue for prolonged radiotherapy for tissue treatment.

2. The ablation apparatus system of claim 1, wherein the biocompatible material for the coating is a biodegradable material.

3. The ablation apparatus system as in claim 1 further comprising at least one temperature sensor, wherein the temperature sensor is disposed at close proximity of the wire distal end.

4. The ablation apparatus system as in claim 1 further comprising at least one temperature sensor, wherein the temperature sensor is disposed on the elongated metallic tube.

5. The apparatus system as in claim 3 or 4 further comprising temperature control means for controlling a temperature sensed from the at least one temperature sensor, wherein the temperature measured from the temperature sensor is relayed to the temperature control means and is adapted to effect the radiofrequency current delivery to the vascular stent.

6. The ablation apparatus system of claim 1, wherein the radiofrequency current is within the range of 50 to 2,000 kHz.

7. The ablation apparatus system of claim 1, wherein the detachable conducting wire means is selected from the group consisting of a guidewire, a spiral wire, a catheter wire, a catheter probe having an electrical conducting wire, and a combination thereof.

8. The ablation apparatus system of claim 1, wherein the biocompatible material for the coating is a thermally degradable material.

9. A method of preventing restenosis of a blood vessel which has undergone angioplasty to open a restricted region of a lumen of the vessel, the method comprising inserting a stent into the blood vessel and deploying the stent to contact the vessel wall at the site of the restricted region; irradiating the tissue in the wall at said site with a radioactive substance in a coated layer which is coated to an exterior surface of the stent; and providing radiofrequency current from a radiofrequency current generator to the stent and heat to the surrounding vessel wall through an electrical conducting wire so that the radioactive substance diffuses more quickly into the heated tissue for prolonged radiotherapy.

10. The method of preventing restenosis of a blood vessel as in claim 9, the method further comprising the stent having a coated layer composed of thermally degradable material so that the radioactive substance is being embedded in the tissue in the wall.

11. The method of preventing restenosis of a blood vessel as in claim 9, the method further comprising the electrical conducting wire having a temperature sensor, wherein the temperature sensor is disposed at a distal end of the electrical conducting wire.

12. The method of preventing restenosis of a blood vessel as in claim 10, the method further comprising the radiofrequency current generator having a temperature control means, wherein a temperature measured from the temperature sensor is relayed to the temperature control means and adapted to effect the radiofrequency current delivery to the stent.

13. The method of preventing restenosis of a blood vessel as in claim 9, the method further comprising the radiofrequency current generator having the radiofrequency current within the range of 50 to 2,000 kHz.

14. The method of preventing restenosis of a blood vessel as in claim 9, wherein the electrical conducting wire is selected from the group consisting of a guidewire, a spiral wire, a catheter wire, a catheter probe having an electrical conducting wire, and a combination thereof.

15. A method for treating tissues of a patient having a metallic implant, said metallic implant having a thin coating on an exposed surface of said implant and said coating including a carrier composed of a biocompatible material and having dispersed therein a radioactive substance that diffuses readily in contact with heated tissue;
the method comprising the steps of:

(a) inserting detachable conducting wire means for detachably contacting said metallic implant, said detachable conducting wire means having a wire distal end and a wire proximal end, wherein the wire distal end is to contact the metallic implant and the wire proximal end is to be coupled to a radiofrequency current source; and (b) applying radiofrequency current from a radiofrequency current generating means to the metallic implant through the detachable conducting wire means so that the radioactive substance diffuses more quickly into the heated tissue for prolonged radiotherapy.

16. The method for treating tissues of a patient having a metallic implant as in claim 15, wherein the metallic implant is a stent.

17. The method for treating tissues of a patient having a metallic implant as in claim 15, wherein the metallic implant has a coated layer composed of thermally degradable material so that the radioactive substance is being embedded in the tissue.

18. The method for treating tissues of a patient having a metallic implant as in claim 15, wherein the detachable conducting wire means comprises a temperature sensor disposed at a distal end of the detachable conducting wire means.

19. The method for treating tissues of a patient having a metallic implant as in claim 15, wherein the radiofrequency current generating means comprises temperature control means, wherein a temperature measured from the temperature sensor is relayed to the temperature control means and adapted to effect the radiofrequency current delivery to the metallic implant.

20. The method for treating tissues of a patient having a metallic implant as in claim 15, wherein the radiofrequency current generating means has the radiofrequency current within the range of 50 to 2,000 kHz.

* * * * *